US005972860A

United States Patent [19]

Eshita et al.

[11] Patent Number: 5,972,860

[45] Date of Patent: Oct. 26, 1999

[54] FRAMED SOAP COMPOSITION CONTAINING NON-IONIC SURFACTANT AND INORGANIC SALT

[75] Inventors: Yoshiyuki Eshita; Manabu Tonomura; Toshio Nozaki; Hironobu Otani; Takeshi Hasegawa, all of Tokyo, Japan

[73] Assignee: Kao Corporation, Tokyo, Japan

[21] Appl. No.: 08/988,380

[22] Filed: Dec. 10, 1997

[30] Foreign Application Priority Data

Dec. 11, 1996 [JP] Japan .................................... 8-352215

[51] Int. Cl.[6] .............................. A61K 7/50; C11D 17/02

[52] U.S. Cl. .......................... 510/145; 510/152; 510/153; 510/155; 510/141; 510/144

[58] Field of Search .................................... 510/141, 144, 510/145, 152, 153, 155

[56] References Cited

U.S. PATENT DOCUMENTS

| | | | |
|---|---|---|---|
| 3,312,627 | 4/1967 | Hooker et al. | 252/152 |
| 3,351,558 | 11/1967 | Zimmerer | 252/137 |
| 3,835,058 | 9/1974 | White | 252/121 |
| 4,181,632 | 1/1980 | Schebece | 252/542 |
| 4,207,198 | 6/1980 | Kenkare | 252/117 |
| 4,328,131 | 5/1982 | Carson, Jr. et al. | 252/542 |
| 4,439,355 | 3/1984 | Kenkare . | |
| 5,194,172 | 3/1993 | Taneri et al. | 252/130 |
| 5,211,941 | 5/1993 | Komori et al. | 424/70 |
| 5,342,611 | 8/1994 | Komori et al. | 424/70 |
| 5,607,980 | 3/1997 | McAtee et al. | 514/476 |

FOREIGN PATENT DOCUMENTS

| | | |
|---|---|---|
| 0 617 955 | 10/1994 | European Pat. Off. . |
| WO 92/09679 | 6/1992 | WIPO . |

*Primary Examiner*—Yogendra Gupta
*Assistant Examiner*—Necholus Ogden
*Attorney, Agent, or Firm*—Oblon, Spivak, McClelland, Maier & Neustadt, P.C.

[57] ABSTRACT

A framed soap composition comprises (a) from 20 to 50% by weight of a fatty acid soap, (b) from 1 to 15% by weight of a nonionic surfactant, and (c) from 0.1 to 5% by weight of an inorganic salt. A framed soap composition incorporated with air bubbles is produced by melting a mixture containing these components while heating the mixture in the presence of water, subjecting the resultant molten material to aeration treatment to incorporate air bubbles, and pouring the resultant molten material incorporated with air bubbles, into a frame followed by cooling to harden the molten material.

12 Claims, 1 Drawing Sheet

FRAMED SOAP COMPOSITION CONTAINING NON-IONIC SURFACTANT AND INORGANIC SALT

BACKGROUND OF THE INVENTION 1.

Field of the Invention

This invention relates to a framed soap composition having advantages that it may hardly crack and also hardly become swollen, even when any means is taken for its formulation, e.g., activators other than soap are added, in order to attain a preferable feel on use, and also having a high productivity comparable to milled soap. 2.

Description of the Related Art

From differences in production processes, soap can be roughly grouped into two types. One of them is milled soap and the other is framed soap.

The milled soap is obtained by adding a perfume, a dye and so forth to a soap base material obtained by heating and drying neat soap, well mixing them by means of a mixer, putting the resultant mixture to a rolling machine and an extruder to extrude and mold the mixture into bars while kneading and compressing it, and stamping the bar-like molded products thus obtained. The milled soap obtained in this way have advantages that it may readily dissolve in water or the like and also has a high productivity. On the other hand, however, the milled soap has problems that it tends to crack and tends to become swollen. In particular, it greatly tends to become swollen when it has a high water content or when it contains other activators.

As for the framed soap, it is obtained by adding various additives to neat soap, directly pouring the resultant mixture into a frame, and cooling it in the frame to harden, followed by drying. The framed soap obtained in this way is constituted basically of from 50 to 70% by weight of fatty acid soap, from 10 to 20% by weight of polyols (glycerol, etc.) and the balance being water, and has features that it may hardly crack and may hardly become swollen. Also, since it can be produced basically by pouring the neat soap into a frame, it can be produced at a lower cost in view of the cost of production facilities than the cost of production facilities for the milled soap.

The framed soap, however, has disadvantages that it takes at least a day or two days until the soap hardens and dries, and takes as long as about a month in the case of transparent soap, bringing about a problem of a very low productivity. For this reason, under existing circumstances, the framed soap has commercially a very small share except for transparent soap, despite the advantages that it may hardly crack and may hardly become swollen. This is because, as stated above, while it can be produced at a lower cost than the milled soap in view of the cost of production facilities than the cost of production facilities for the milled soap, its final products result in a greatly higher cost of production than the milled soap.

What is called light-weight soap or floating soap, in which air bubbles are entrapped, is also known as a type of the framed soap, see Japanese Patent Application Laid-open No. 4-218599. This publication discloses a floating soap produced by melting a neat soap composed of from 10 to 50% of coconut oil and 50 to 90% of beef tallow and having a water content of from 28 to 35%, introducing the resultant molten material into a high-shear mixing machine, blowing and mixing high-pressure air to incorporate air bubbles into the molten material, pouring into a soap frame the resultant mixture incorporated with air bubbles, and leaving it to cool to harden.

However, the formulation of soap as disclosed in Japanese Patent Application Laid-open No. 4-218599 has caused a problem that the bubbles can not be well retained as they stand to cause phase separation into crushed bubble phase and solid phase to become hard.

SUMMARY OF THE INVENTION

The present invention will solve the above problems the prior art has had. Accordingly, a first object of the present invention is to make it possible to produce framed soap that may hardly crack and may hardly become swollen, in a productivity comparable to that of the milled soap.

A second object of the present invention is to make it possible to produce bubble-entrapped soap in which air bubbles are incorporated at a high volume fraction, which can be readily produced by framing.

The present inventors have discovered that a molten material of a mixture prepared by mixing a fatty acid soap with a nonionic surfactant and an inorganic salt in a specific proportion, melted In the presence of water can be hardened in a short time when this molten material is poured into a frame followed by cooling, and also discovered that such a molten material can be readily treated by aeration using a conventional whipping machine and also the resultant molten material Incorporated with air bubbles can be hardened in a short time as it stands when it is poured into a frame followed by cooling. Thus, they have accomplished the present invention.

As a first embodiment which can achieve the first object, the present invention provides a framed soap composition comprising the following components (a) to (c):

(a) from 20 to 50% by weight of a fatty acid soap;

(b) from 1 to 15% by weight of a nonionic surfactant; and (c) from 0.1 to 5% by weight of an inorganic salt.

As a second embodiment which can achieve the second object, the present invention provides a process for producing a framed soap composition incorporated with air bubbles, comprising the steps of;

melting a mixture containing the following components (a) to (c):

(a) from 20 to 50% by weight of a fatty acid soap;

(b) from 1 to 15% by weight of a nonionic surfactant; and (c) from 0.1 to 5% by weight of an inorganic salt; while heating the mixture in the presence of water to obtain a molten material;

subjecting the molten material to aeration treatment to incorporate air bubbles to obtain a molten material incorporated with air bubbles; and pouring the molten material incorporated with air bubbles, into a frame followed by cooling to harden the molten material.

DETAILED DESCRIPTION OF THE INVENTION

Figure 1:
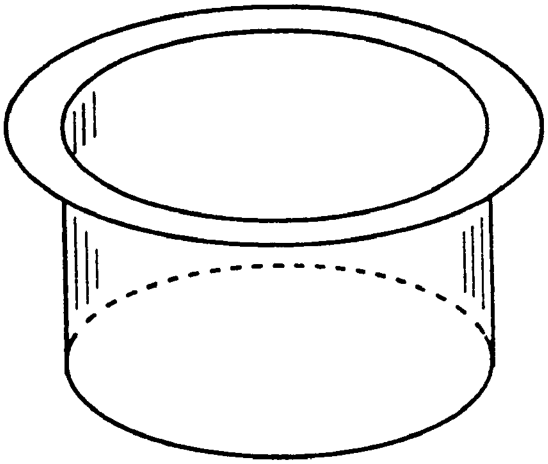
FIG. 1 is a perspective view of a cup-like container used as a soap frame in Example 7.

The present invention will be described below in detail.

According to the first embodiment, the present invention is a framed soap composition comprising the following components (a) to (c):

(a) from 20 to 50% by weight of a fatty acid soap;

(b) from 1 to 15% by weight of a nonionic surfactant; and (c) from 0.1 to 5% by weight of an inorganic salt.

With such formulation, a molten material of a mixture of these, melted in the presence of water can be hardened in a short time when the molten material is poured into a frame followed by cooling, so that a high productivity comparable to that of milled soap can be attained.

The framed soap composition according to the second embodiment of the present invention, having the same formulation as the first embodiment of the present invention, is obtained by whipping the molten material before it is poured into a frame, to make aeration treatment. Such treatment makes the hardening rate much higher. Accordingly, when the molten material in a whipped state is poured into the frame, it can be hardened as it is, without causing phase separation.

In this instance, taking account of the hardening rate, hardness, easy dissolution and so forth of the soap composition, the air bubbles may preferably be in a volume fraction of at least 10%, and more preferably at least 30%. From the viewpoint of the strength of the resultant soap composition, the air bubbles may preferably be in a volume fraction not more than 80%.

As to the size of air bubbles, in order to make the framed soap composition not excessively dissolve and also make it hard to become swollen, the air bubbles may preferably be in an average bubble diameter of 80 $\mu$m or smaller, and more preferably be 60 $\mu$m or smaller. Here are no particular limitations on the lower limit of the average bubble diameter. Taking account of productivity when a conventional whipping machine for industrial use is used, it may preferably be 10 $\mu$m or larger, and more preferably 20 $\mu$m or larger.

As the gas used when the aeration treatment is made, air, nitrogen gas or the like may be used under appropriate selection.

The whipping carried out as described above enables the framed soap composition to have a good white appearance even when any whitener such as titanium oxide is not used. Also, when colored, the soap can have a preferable pale color tone. Moreover, the soap can be well fragrant when used, making it possible to use perfumes in a smaller quantity. Furthermore, the properties of being hard to crack and the properties of being hard to become swollen which are inherent in framed soap compositions can be ensured.

The component—(a) fatty acid soap used in the first and second embodiments of the present invention may include those selected from the group consisting of alkali metal salts (e.g., sodium salt and potassium salts), ammonium salts or alkanol amine salts (e.g., monoethanolamine salts, diethanolamine salts and diethanolamine salts) of saturated or unsaturated fatty acids having 8 to 22 carbon atoms. In particular, the component—(a) fatty acid may preferably contain an alkali metal salt, especially, a sodium salt of a saturated fatty acid in a proportion of at least 80% by weight, because the soap composition may harden with difficulty if the saturated fatty acid is in a small proportion in the component—(a) fatty acid soap. Here, in order to improve lathering properties of the framed soap composition, the component—(a) fatty acid soap may preferably contain lauric acid soap in a proportion of at lest 25% by weight.

The fatty acid constituting the component—(a) fatty acid soap may include those obtained from vegetable fats and oils or animal fats and oils, e.g., palm oil, palm kernel oil, coconut oil, castor oil, soy bean oil, cotton seed oil, rapeseed oil, sunflower oil, beef tallow and lard. In particular, palm kernel oil or coconut oil is preferred. In this instance, these fats and oils may preferably be previously subjected to hydrogenation so that they can have a low degree of unsaturation.

The component—(a) fatty acid soap can be produced by direct saponification of the above fats and oils or by neutralization of free fatty acids separately prepared.

The component—(a) fatty acid soap must be contained in the framed soap composition in an amount of at least 20% by weight, taking account of lathering properties and hardening properties. If it is in a too large content, other components relatively come to be in a too small content to obtain the desired properties. Hence, it should be in a content up to 50% by weight, and may preferably be in a content of from 25 to 45% by weight.

The component—(b) nonionic surfactant used in the first and second embodiments of the present invention is used in order to accelerate the hardening of the soap composition, and may be used under appropriate selection from known nonionic surfactants. In particular, preferred nonionic surfactants may Include polyoxyethylene (POE) fatty acid esters and polyoxyethylene alkyl ethers, and may specifically include compounds having as a hydrophilic group a polyoxyethylene group having an average number of EO (ethylene oxide) addition moles of from 6 to 150, and preferably from 10 to 50. Of such compounds, compounds having as a hydrophobic group an alkyl group having 10 to 18 carbon atoms, preferably 12 to 14 carbon atoms, and having an HLB (hydrophilic-lipophilic balance) value of 8 or more, and preferably 10 or more, are preferred. For example, as preferred examples, they may include EMANONE 1112 (polyethylene glycol(12) monolaurate available from Kao Corporation; HLB: 14.8), EMULGEN 123P (polyethylene(23) lauryl ether available from Kao Corporation; HLB: 16.9), and EMALEX 730 (polyethylene (30) lauryl ether available from Nihon Emulsion Co., Ltd.; HLB: 18).

The component—(b) nonionic surfactant may be contained in the framed soap composition in an amount of from 1 to 15% by weight, and preferably from 2 to 4% by weight.

The component—(a) fatty acid soap and the component—(b) nonionic surfactant may preferably be contained in a ratio ranging from 1:25 to 1:5, and more preferably 1:20 to 1:10. If the fatty acid soap is in a too large content with respect to the nonionic surfactant, its addition can be effective with difficulty, and, if in a too small content, the soap composition can not have a sufficient hardness.

The component—(c) inorganic salt used in the first and second embodiments of the present invention imparts a good fluidity to the soap composition when the molten material for the framed soap composition is poured into the frame. As a preferable inorganic salt, it may include sodium chloride. The component—(c) inorganic salt may be contained in the framed soap composition in an amount of from 0.1 to 5% by weight, and preferably from 1 to 4% by weight. If it is less than 0.1% by weight, crystals of soap may grow in the form of fibers to cause an increase in viscosity to provide no intended fluidity. If more than 5% by weight, the lathering properties may lower undesirably.

In addition to the above components, the framed soap compositions according to the first and second embodiments of the present invention may preferably contain a polyol, e.g., glycerol, sorbitol, xylitol, mannitol, sucrose, glucose, trehalose, polyethylene glycol, polypropylene glycol and water-soluble polymers. The polyol can improve the stability of air bubbles present in the molten material of the components (a) to (b). Such a polyol may preferably be contained in the framed soap composition in an amount of from 5 to 40% by weight, and more preferably from 20 to 30% by weight. If it is in a too small content, the air bubbles can not be made well stable, and, if it is in a too large content, the soap composition may harden with difficulty.

In the case of the framed soap composition according to the second embodiment of the present invention, a hydroxy acid ester type surfactant, a monoglyceride type surfactant, a sucrose ester type surfactant or a lactic acid ester type surfactant may preferably be added so that the whipped soap composition poured into the frame may not undergo bubble breakage to cause separation of liquid phase. In particular, it is preferable to add a lactic acid ester type surfactant. Any of these ester type surfactants may preferably be contained in the framed soap composition in an amount of from 1 to 10% by weight, and more preferably from 2 to 5% by weight. If it is in a too small content, the whipped composition tends to undergo bubble breakage, and, if it is in a too large content, the production cost may become higher than the practical level.

To the framed soap compositions according to the first and second embodiments of the present invention, a non-soap type anionic surfactant may preferably be added in order to improve lathering properties at low temperature and dispersion of scum. Such an anionic surfactant may include alkanoyl isethionate, polyoxyethylene ether sulfate, methyl taurate, sarcocinate, sulfosuccinate, monoalkyl phosphate and alkanoyl- β-alanine salts, any of which may be used. The non-soap type anionic surfactant may preferably be contained in the framed soap composition in an amount of from 1 to 20% by weight, and more preferably from 5 to 15% by weight. If it is in a too small content or in a too large content, the lathering properties at low temperature and dispersion of scum can not be improved.

The framed soap composition of the present invention may also preferably be mixed with a free fatty acid in order to make the soap mild and to improve its lathering properties. As the free fatty acid, hardened coconut oil fatty acid or the like may be used. The free fatty acid may preferably be contained in the framed soap composition in an amount of from 0.2 to 9% by weight, and more preferably from 0.5 to 5% by weight. If it is in a too small content, the soap can no be well made mild and improved in the lathering properties, and, if it is in a too large content, the soap can not lather.

Here, the component—(a) fatty acid soap and the free fatty acid may preferably be contained in a ratio ranging from 99:1 to 85:15, and more preferably 97:3 to 90:10.

The framed soap composition of the present invention may also preferably be mixed with an organic acid other than the fatty acids in order to make its fragrance stable. Such an organic acid may include lactic acid and gluconic acid. The organic acid may preferably be contained in the framed soap composition in an amount of from 0.01 to 3% by weight, and more preferably from 0.1 to 1% by weight. If it is in a too small content, it can not be well effective, and, if it is in a too large content, its addition can no longer be expected to be effective enough for its content.

Besides the foregoing, when the framed soap composition of the present invention is produced, water must be mixed in order to bring into a uniform molten material the components (a) to (c) and other components optionally added. The water may usually be mixed in an amount of from 25 to 40% by weight. Since the framed soap composition of the present invention rapidly harden after it has been made up, this water is contained in it in substantially the same proportion immediately after its production, but gradually decreases with drying.

In addition to the components described above, known additives as used in conventional framed soap compositions may be added to the framed soap composition of the present invention, as exemplified by an antimicrobial agent, a perfume, a pigment, a dye, an oil and other low-irritative agents. Here, the antimicrobial agent may include trichlosan and trichlorocarbanilide, which may usually be mixed in an amount of from 0.1 to 2% by weight. The perfume, pigment or dye may usually be mixed in an amount of from 0.2 to 5% by weight. The oil may include lanolin, paraffin oil, vaseline and isopropyl myristate, which may usually be mixed in an amount of from 0.5 to 5% by weight.

The framed soap composition of the present invention can be produced by conventional methods. For example, it can be produced by melting or dissolving the components (a) to (c) and other optional components while heating them to 65 to 80° C. with stirring, and pouring the resultant molten material or solution into a frame as it is, followed by cooling and drying.

Especially when the light-weight (floating) soap is produced by incorporating air bubbles, it can be produced by subjecting the molten material thus obtained, to aeration treatment using a whipping machine for domestic use or industrial use to incorporate air bubbles, and pouring into a frame the resultant molten material incorporated with air bubbles, followed by cooling to harden and further optionally followed by drying.

EXAMPLES

Examples 1 to 5 & Comparative Examples 1 to 4

The components formulated as shown in Tables 1 and 2 were melted while heating them at 76° C. The molten materials obtained were each poured into a conventional soap frame without making aeration treatment, and then left to cool to harden. Thus, framed soap compositions were prepared.

TABLE 1

(wt. %)

| Components | Example 1 | 2 | 3 | 4 | 5 |
|---|---|---|---|---|---|
| Sodium laurate | 33.3 | 32.0 | 15.0 | 32.2 | 43.0 |
| Sodium myristate | — | — | 15.0 | — | — |
| POE lauryl ether Na sulfate | 1.0 | 0.0 | 0.0 | 9.6 | 11.4 |
| Sodium cocoyl isethionate | 2.0 | 5.0 | 2.0 | — | — |
| Sodium lauroyl lactylate | 4.0 | 0.0 | 4.5 | — | — |
| POE monolaurate*1 | 2.0 | 2.0 | 2.5 | 2.0 | 2.4 |
| Lactic acid (90%) | — | — | — | 0.1 | 0.1 |
| Lauric acid | 0.5 | 6.0 | 3.0 | 4.6 | 4.5 |
| Myristic acid | — | — | 3.0 | — | — |
| Glycerol | 17.0 | 14.6 | 15.0 | 9.0 | 17.6 |
| Sorbitol | 3.0 | 3.5 | 4.0 | 4.3 | 0.0 |
| Sodium chloride | 2.0 | 2.0 | 1.5 | 1.0 | 1.8 |
| Xanthane rubber | — | — | — | 0.1 | 0.0 |
| Perfume | 0.6 | 1.0 | 1.5 | 1.1 | 0.8 |
| Water | 34.6 | 33.9 | 33.0 | 25.9 | 18.5 |

Remarks:
*1 The number of EO addition moles of POE monolaurate: 12

TABLE 2

(wt. %)

| Components | Comparative Example 1 | 2 | 3 | 4 |
|---|---|---|---|---|
| Sodium laurate | 42.6 | 32.1 | 35.0 | 40.0 |
| Sodium myristate | — | — | 10.0 | — |

TABLE 2-continued (wt. %)

| Components | Comparative Example 1 | 2 | 3 | 4 |
|---|---|---|---|---|
| Sodium stearate | — | — | — | 20.0 |
| POE lauryl ether Na sulfate | 0.0 | 8.4 | 0.0 | 5.0 |
| Sodium lauroyl lactylate | — | — | 4.0 | — |
| POE monolaurate*1 | 0.0 | 0.0 | 2.0 | 2.0 |
| Lauric acid | 1.6 | 1.1 | 3.0 | 0.0 |
| Glycerol | 13.8 | 18.0 | 15.3 | 10.0 |
| Sorbitol | 0.0 | 0.0 | 0.0 | 0.0 |
| Sodium chloride | 2.0 | 2.0 | 0.0 | 0.0 |
| Perfume | 1.0 | 1.1 | 1.0 | 1.0 |
| Water | 39.0 | 37.3 | 29.7 | 22.0 |

Remarks:
*1 The number of EO addition moles of POE monolaurate: 12

Evaluation

With regard to the framed soap compositions of Examples 1 to 5 and Comparative Examples 1 to 4, "hardening rate", "soap hardness after cooling" and "lathering on use" were examined and evaluated in the manner as described below. Results obtained are shown in Table 3.

Hardening Rate

Neat soap melted at 80 was poured into a 30 ml plastic cup (a frame). After making sure of its fluidity, it was left at room temperature for 5 minutes. Thereafter, the framed soap obtained was removed from the frame to visually observe whether or not it deformed when removed. As evaluation criteria, an instance where the molten neat soap was poured into the frame faithfully after its shape and also did not flow or deform after cooling was evaluated as "proper".

Soap Hardness After Cooling

According to the vulcanized rubber hardness test method of JIS K6253, a hardness of from 45 degrees to 80 degrees was noted as "sufficient", and 80 degrees or higher, as "hard".

Lathering on Use

Five expert panelists washed their hands to make evaluation. An instance where the soap lathered better than conventional general-purpose milled soaps was indicated as "AA"; an instance where it lathered almost alike, as "A"; an instance where it lathered worse, as "B"; and an instance where it lathered very worse, as "C".

TABLE 3

| | Hardening rate | Soap hardness after cooling | Lathering on use |
|---|---|---|---|
| Example: | | | |
| 1 | proper | hard | A |
| 2 | proper | sufficient | A |
| 3 | proper | sufficient | AA |
| 4 | proper | sufficient | AA |
| 5 | proper | sufficient | AA |
| Comparative Example: | | | |
| 1 | low | hard | B |
| 2 | low | soft | B |
| 3 | hardly fluid | sufficient | B |
| 4 | hardly fluid | hard | C |

As can be seen from Table 3, the framed soap compositions of Examples 1 to 5 showed superior results in respect of all the "hardening rate", "soap hardness after cooling" and "lathering on use". Also, the framed soap compositions of Examples 1 to 51 thus obtained, were hard to crack and yet hard to become swollen.

On the other hand, in the case of the framed soap compositions of Comparative Examples 1 and 2, in which the component—(b) nonionic surfactant is not contained, they are seen not to be well improved in the hardening rate. In the case of the framed soap compositions of Comparative Examples 3 and 4, in which the component—(c) inorganic salt is not contained, they are seen to be unable to achieve a sufficient fluidity when the molten soap compositions are poured into the frame. Also, the framed soap compositions of Comparative Examples 1 to 4 tended to become swollen. Thus, the framed soap compositions of Comparative Examples 1 to 4 were hard to produce, and were substantially not feasible for commercialization in view of lathering properties and hardness.

Example 6 & Comparative Examples 5 to 7

The components formulated as shown in Table 4 were melted while heating them at 80° C. The molten materials obtained were each whipped by batch processing using a domestic whipping machine to make aeration treatment until each came to have a volume of 1.7 times. The material thus whipped was poured into a conventional soap frame, and then left to cool to harden. Thus, framed soap compositions incorporated with air bubbles were prepared.

During the whipping, the temperature dropped by 5 to 8° C., and the temperature at which the molten material was started to harden was about 65° C. To leave 100 ml of the whipped soap composition to cool and harden, it was left for 30 minutes to thereby cool to 40° C. or below.

With regard to the framed soap compositions of Example 6 and Comparative Examples 5 to 7, "whipping", "hardening rate", "deformation" and "phase separation" were evaluated in the manner as described below. Results obtained are shown in Table 5.

Whipping

The state during aeration treatment was visually observed to judge whether or not the whipping was easy and was possible.

Hardening Rate

An instance where the molten soap composition did not harden when its temperature was lowered by 10° C. while whipping, but hardened in 10 minutes when its temperature was further lowered, was evaluated as "proper". An instance where the molten soap composition did not harden when its temperature was lowered by 10° C. while whipping, and finally hardened in 10 minutes when its temperature was further lowered, but was standing over-cooled and did not hardened in 10 minutes, was evaluated as "slow hardening". An instance where the molten soap composition hardened up when its temperature was lowered by 10° C. while whipping was evaluated as "too rapid hardening".

Deformation

Neat soap melted at 80° C. was poured into a 30 ml plastic cup (a frame). After making sure of its fluidity, it was left at room temperature for 5 minutes. Thereafter, the framed soap obtained was removed from the frame to visually observe whether or not it deformed when removed. As evaluation criteria, an instance where the molten neat soap was poured into the frame faithfully after its shape and also did not flow or deform after cooling was evaluated as "proper". An instance where the molten neat soap came to have a shape greatly different from the frame when molded, or became greatly holed or became greatly hollow, was evaluated as "deformed". An instance where it did not harden was evaluated as "unconfirmable".

Phase Separation

An instance where a bubble-free phase was formed at the bottom of the frame to look colored was evaluated as "phase-separated". An instance where a clear separating boundary line was visually recognizable was evaluated as "greatly phase-separated".

TABLE 4

(wt. %)

| Components | Example 6 | Comparative Example 5 | Comparative Example 6 | Comparative Example 7 |
|---|---|---|---|---|
| Sodium laurate | 40.0 | 35.0 | 30.0 | 30.0 |
| Sodium myristate | — | 10.0 | 10.0 | 25.0 |
| POE lauryl ether Na sulfate | 1.0 | — | — | — |
| Sodium cocoyl isethionate | 1.0 | — | 2.0 | 6.0 |
| Sodium lauroyl lactylate | — | 4.0 | — | 4.5 |
| POE monolaurate*1 | 2.0 | 2.0 | — | 2.5 |
| Lauric acid | 0.5 | 3.0 | 0.5 | 3.0 |
| Myristic acid | — | — | — | 3.0 |
| Glycerol | 17.0 | 15.3 | 17.0 | 15.0 |
| Sorbitol | 3.0 | — | 3.0 | 4.0 |
| Sodium chloride | 2.0 | — | 2.0 | 1.5 |
| Perfume | 0.5 | 1.0 | 1.4 | 1.5 |
| Water | 33.0 | 29.7 | 34.6 | 8.0 |

Remarks:
*1 The number of EO addition moles of POE monolaurate: 12

TABLE 5

| | Whinning | Hardening rate | Deformation | Phase separation |
|---|---|---|---|---|
| Example: | | | | |
| 6 | easy | proper | none | none |
| Comparative Example: | | | | |
| 5 | difficult | hardened during whipping | none | none |
| 6 | difficult | slow | holes of 10 mm deep | greatly phase-separated |
| 7 | impossible | proper | unconfirmable | — |

As can be seen from Table 5, the framed soap composition of Example 6 showed superior results in respect of all the "whipping", "hardening rate", "deformation" and "phase separation". Also, the framed soap composition of Example 6, thus obtained, was hard to crack and yet hard to become swollen.

On the other hand, in the case of the framed soap composition of Comparative Example 5, in which the component—(c) inorganic salt was not contained, the hardening rate was so high as to make whipping itself difficult, and the molten material hardened up during whipping. Also, the framed soap composition of Comparative Example 6, in which the component—(b) nonionic surfactant was not contained, was difficult to whip and also showed a low hardening rate. It also tended to deform and moreover showed a great phase separation. In the case of the framed soap composition of Example 7, in which the water was in an excessively small content and relatively the component—(a) fatty acid soap was in a large content, bubbles were unstable and consequently the whipping was impossible. Also, the framed soap compositions of Comparative Examples 5 to 7 tended to become swollen and had unpreferable hardness and appearance.

Example 7

The relationship between the average bubble size and the swolleness, lathering properties and rubbing solubility of soap was examined using the framed soap composition formulated in Example 3.

More specifically, the components as formulated in Example 3 were melted by heating and mixing them at 75° C. The resultant molten material (flow rate: 19.7 kg/hr), a perfume (flow rate: 0.3 kg/hr) and nitrogen gas (flow rate: 13 Nl/hr) were continuously fed to an industrial whipping machine (foaming machine Model MDFO, manufactured by Ebara Seisakusho) to carry out aeration treatment at a number of revolution of 500 rpm, 100 rpm, 75 rpm or 50 rpm. The composition thus obtained was poured into a cup-like container (volume: 100 cc) like the one shown in FIG. 1, which was then put in a −15° C. refrigerator for 15 minutes to allow to harden.

Figure 2:
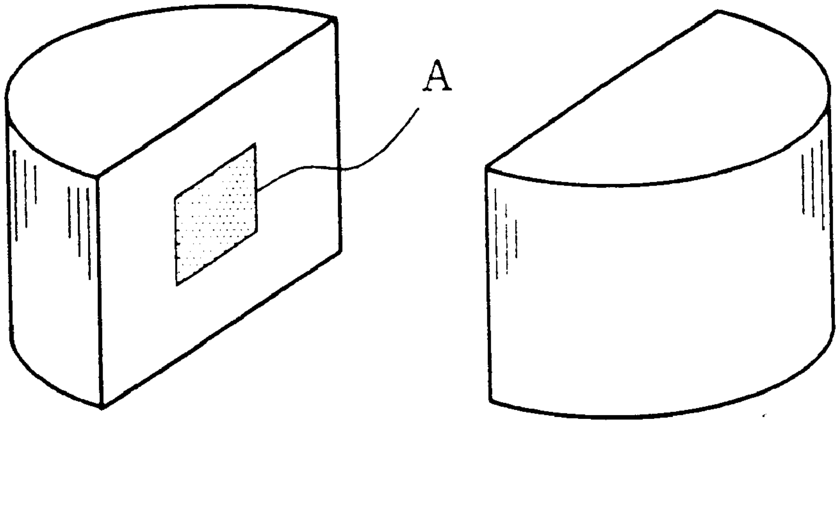
FIG. 2 illustrates how the framed soap composition prepared in Example 7 stands in its cross section.

After it hardened, the soap incorporated with air bubbles was taken out of the cup-like container, and then cut into two pieces as shown in FIG. 2. Filmy sample A of about 2 cm square was sampled from one cut surface, and cell diameters of 1,000 air bubbles were measured to calculate an average bubble size thereof. Results obtained are shown in Table 6.

With regard to the remaining piece of the soap cut off, rubbing solubility ($g/cm^2$) was measured according to JIS K3304 ("Soap Testing Method" 1956). Results obtained are shown in Table 6. Numerical values of the rubbing solubility have the following qualitative meaning.

It means that when the rubbing solubility ($g/cm^2$) is less than 4, the solubility is too small; when not less than 4 to less than 7, the solubility is a little small; when not less than 7 to less than 10, the solubility is appropriate; when not less than 10 to less than 14, the solubility is a little great; and when not less than 14, the solubility is too great.

With regard to the other piece of the soap cut off, a swolleness test was made in the manner as described below: The cut surface of the other piece of the soap cut off was immersed in 25° C. water for 1 hour, and thereafter taken out to allow it to stand overnight in a desiccator of 100% humidity. The soap was taken out of the desiccator, and a plunger penetration test (JIS K6253 "vulcanized rubber hardness test method") was made on the face immersed in the water to make evaluation as a swolleness test according to the following evaluation criteria. Results obtained are shown in Table 6.

Evaluation Criteria

| Rank | Criteria |
|---|---|
| AA: | Having a sufficient hardness. |
| A: | Having substantially a sufficient hardness. |
| B: | Soft, but no problem in practical use. |
| C: | Soft and flimsy, having a problem in practical use. |

Lathering properties were also examined and evaluated in the same manner as in Example 1. Results obtained are shown in Table 6.

TABLE 6

| | Number of revolution of whipping machine | | | |
|---|---|---|---|---|
| Evaluation item | 500 rpm | 100 rpm | 75 rpm | 50 rpm |
| Average bubble size: ($\mu$m) | 58 | 79 | 109 | 125 |
| Rubbing solubility: (g/cm$^2$) | 7.9 | 10.0 | 14.5 | 16.0 |
| Swolleness test: | AA | A | B | B |
| Lathering properties: | AA | AA | AA | AA |

As can be seen from the results of Example 7, the soap tends to become swollen with an increase in the average bubble size. As also can be seen therefrom, a preferable average bubble size is 80 $\mu$m or smaller.

As described above, according to the present invention, a framed soap that may hardly crack and may hardly become swollen can be produced In a productivity comparable to that of the milled soap. Also, a bubble-entrapped soap in which air bubbles are incorporated at a high volume fraction can be readily produced by framing.

What is claimed is:

1. A framed soap composition comprising the following components (a) to (d):

(a) from 20 to 50% by weight of a fatty acid soap;

(b) from 1 to 15% by weight of a nonionic surfactant;

(c) from 0.1 to 5% by weight of an inorganic salt; and (d) from 25 to 40% by weight of water, wherein the component—(b) nonionic surfactant is a polyoxyethylene fatty acid ester or a polyoxyethylene alkyl ether.

2. The framed soap composition according to claim 1, wherein the component—(a) fatty acid soap contains a sodium salt of a saturated fatty acid in a proportion of at least 80% by weight.

3. The framed soap composition according to claim 1, wherein the component—(a) fatty acid soap contains lauric acid soap in a proportion of at least 25% by weight.

4. A framed soap composition comprising the following components (a) to (d):

(a) from 20 to 50% by weight of a fatty acid soap;

(b) from 1 to 15% by weight of a nonionic surfactant;

(c) from 0.1 to 5% by weight of an inorganic salt; and (d) from 25 to 40% by weight of water, wherein the component—(b) nonionic surfactant is a compound having as a hydrophilic group a polyoxyethylene group having an average number of ethylene oxide addition moles of from 6 to 150.

5. The framed soap composition according to claim 1, wherein the compound having as a hydrophilic group a polyoxyethylene group having an average number of ethylene oxide addition moles of from 6 to 150 is a compound having as a hydrophobic group an alkyl group having 10 to 18 carbon atoms and is a compound having a value of hydrophilic-lipophilic balance of 8 or more.

6. The framed soap composition according to any one of claims 1, 2, 3, 5 and 6, which is incorporated with air bubbles in a volume fraction of at least 10%.

7. The framed soap composition according to claim 6, which is incorporated with air bubbles in a volume fraction of at least 30%.

8. The framed soap composition according to claim 6, wherein the air bubbles incorporated therein has an average diameter of 80 $\mu$m or smaller.

9. The framed soap composition according to claim 6, which further comprises from 0.2 to 9% by weight of a free fatty acid; said component—(a) fatty acid soap and said free fatty acid being contained in a ratio ranging from 99:1 to 85:15.

10. A process for producing a framed soap composition incorporated with air bubbles, comprising the steps of:

melting a mixture containing the following components (a) to (c):

(a) from 20 to 50% by weight of a fatty acid soap;

(b) from 1 to 15% by weight of a nonionic surfactant; and (c) from 0.1 to 5% by weight of an inorganic salt while heating the mixture in the presence of (d) from 25 to 40% by weight of water to obtain a molten material;

subjecting the molten material to aeration treatment to incorporate air bubbles to obtain molten material incorporated with air bubbles; and pouring the molten material incorporated with air bubbles, into a frame followed by cooling to harden the molten material, wherein the component—(b) nonionic surfactant is a polyoxyethylene fatty acid ester or a polyoxyethylene alkyl ether.

11. The framed soap composition according to claim 1 wherein the component (b), nonionic surfactant, is a polyoxyethylene fatty acid ester.

12. The framed soap composition according to claim 1, wherein the component (b) nonionic surfactant, is a polyoxyethylene laurate having from 10 to 50 average number of addition moles of ethylene oxide.

* * * * *

UNITED STATES PATENT AND TRADEMARK OFFICE

CERTIFICATE OF CORRECTION

PATENT NO. : 5,972,860

DATED : October 26, 1999

INVENTOR(S) : Yoshiyuki ESHITA, et al.

It is certified that error appears in the above-identified patent and that said Letters Patent is hereby corrected as shown below:

On the title page, item [75], the fourth inventor's name should be:

--Hironobu Ohtani--

Signed and Sealed this

First Day of August, 2000

Attest:

Q. TODD DICKINSON

*Attesting Officer* *Director of Patents and Trademarks*